(12) United States Patent
Koljonen

(10) Patent No.: US 6,768,812 B1
(45) Date of Patent: Jul. 27, 2004

(54) METHOD FOR LOCATING FEATURES ON AN OBJECT USING VARIED ILLUMINATION

(75) Inventor: Juha Koljonen, Needham, MA (US)

(73) Assignee: Cognex Corporation, Natick, MA (US)

( * ) Notice: Subject to any disclaimer, the term of this patent is extended or adjusted under 35 U.S.C. 154(b) by 0 days.

(21) Appl. No.: 09/538,939

(22) Filed: Mar. 31, 2000

Related U.S. Application Data

(60) Provisional application No. 60/136,172, filed on May 27, 1999.

(51) Int. Cl.[7] ................................................ G06K 9/00
(52) U.S. Cl. ..................................................... 382/150
(58) Field of Search ................................ 382/145, 149, 382/150, 154; 29/833; 250/205, 227.29, 201.1, 203.2, 203.3, 204; 348/87, 126

(56) References Cited

U.S. PATENT DOCUMENTS

| 5,097,516 | A | * | 3/1992 | Amir ............................ 382/274 |
| 5,214,712 | A | * | 5/1993 | Yamamoto et al. .......... 382/149 |
| 5,311,598 | A | * | 5/1994 | Bose et al. ................... 382/149 |
| 5,459,547 | A | * | 10/1995 | Shiozawa ..................... 355/67 |
| 5,532,739 | A | * | 7/1996 | Garakani et al. ............. 348/87 |
| 5,545,901 | A | * | 8/1996 | Pentoney et al. ............ 250/458.1 |
| 5,761,336 | A | | 6/1998 | Xu et al. |
| 5,912,984 | A | | 6/1999 | Michael et al. |
| 5,949,901 | A | * | 9/1999 | Nichani et al. .............. 382/149 |
| 5,982,927 | A | | 11/1999 | Koljonen |
| 6,134,342 | A | | 10/2000 | Doke et al. |
| 6,134,343 | A | * | 10/2000 | Nichani ....................... 382/141 |
| 6,163,374 | A | | 12/2000 | Otani et al. |
| 6,236,747 | B1 | * | 5/2001 | King et al. .................. 382/149 |
| 6,259,827 | B1 | | 7/2001 | Nichani |
| 6,298,149 | B1 | | 10/2001 | Nichani et al. |
| 6,317,513 | B2 | | 11/2001 | Michael et al. |
| 6,330,354 | B1 | * | 12/2001 | Companion et al. ........ 382/150 |
| 6,445,812 | B1 | | 9/2002 | Lai et al. |

* cited by examiner

*Primary Examiner*—Daniel Mariam
*Assistant Examiner*—Shefali Patel

(57) ABSTRACT

A method is provided for locating features of an object using varied lighting. An object is illuminated and a first digital image of the object is acquired. An illumination of the object is varied and a second digital image of the object is acquired while a camera and the object are in a same position as the camera and the object were during the acquiring of the first digital image. One of the first and the second digital image is subtracted from another of the first and the second digital image to produce a difference image. At least one feature of the object is located based on the difference image.

6 Claims, 7 Drawing Sheets

METHOD FOR LOCATING FEATURES ON AN OBJECT USING VARIED ILLUMINATION

This application claims priority to provisional application No. 60/136,172, filed in the U.S. Patent and Trademark Office on May 27, 1999, the contents of which is hereby incorporated by reference.

BACKGROUND OF THE INVENTION

1. Field of Invention

Aspects of the present invention relate to machine vision methods for locating features on an object using varied illumination.

2. Description of Background Information

A vision tool exists that measures the area and location of solder paste printed on circuit boards for the purpose of inspecting the prints made for solder paste screen printing machines. The method used compares a pre-print image of the circuit board at a given inspection site with a post-print image of the circuit board at the given inspection site to determine which pixels in the post-print image are solder paste. An inspection site can be, for example, an entire circuit board or a sub-part of a circuit board depending upon a field of view of the optics used. The identified pixels are then grouped into regions and measured by a "blob" tool.

The main limitation of the above method is that two images of each inspection site of each circuit board must be acquired—a before printing image and an after printing image. Moving the camera from inspection site to inspection site takes time and reduces the throughput of the method.

SUMMARY

In an embodiment of the invention, a method is provided for locating features of an object using varied lighting. An object is illuminated and a first digital image of the object is acquired. An illumination of the object is varied and a second digital image of the object is acquired while a camera and the object are in a same position as were the camera and the object during the acquisition of the first digital image. One of the first and the second digital images is subtracted from another of the first and the second digital images to produce a difference image. At least one feature of the object is located based on the difference image.

BRIEF DESCRIPTION OF THE DRAWINGS

The above and other objects, features, and advantages of the present invention are further described in the Detailed Description which follows, with reference to the drawings by way of non-limiting exemplary embodiments of the invention, wherein.

DETAILED DESCRIPTION

Different regions on printed circuit boards respond differently to lighting changes. For example, solder paste responds differently to lighting changes than does bare circuit board or pads.

Figure 1:
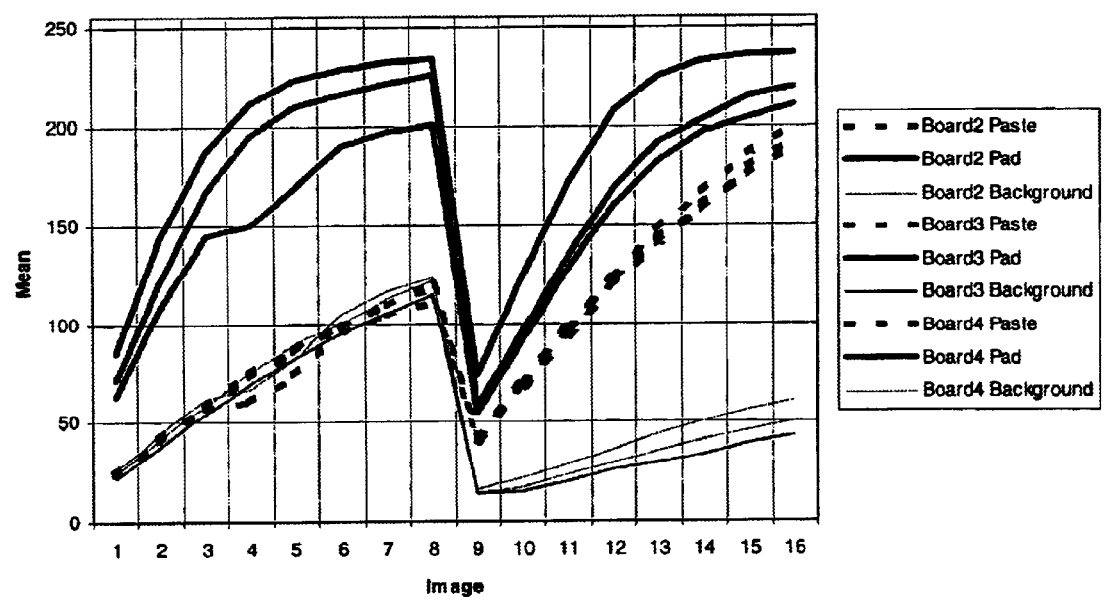
FIG. 1 is a chart showing a difference in light reflectivity properties of a printed circuit board, solder paste and background.

Values one through 8 on the horizontal axis of FIG. 1 depict the lighting response of pads, paste, and boards to continually increasing on-axis illumination while holding off-axis lighting at zero. Values 9 through 16 on the horizontal axis of FIG. 1 depict the lighting response of pads, paste and boards to continually increasing off-axis illumination while holding the on-axis lighting at zero. The vertical axis represents the grey values of the pads, paste or boards, where 0 is dark and 250 is light. Using these lighting conditions, the graph shows the lighting response of 300 random sample points taken from the same locations in different regions on three different circuit board samples.

For each type of material there are trends of behavior for increasing illumination on-axis as opposed to increasing illumination off-axis.

For example, the pads change under both lighting conditions (increasing on-axis light and increasing off-axis light) with a tendency to be brighter with on-axis lighting when observed from a vantage point of a camera. This occurs because pads are reflective, like mirrors, and will reflect on-axis light back into the camera. Off-axis light will be reflected at an incident angle away from the camera.

Similar to pads, the board reflects light less from increasing off-axis lighting than from on-axis lighting, such that the measured grey level of the board exposed to off-axis light is less than the measured grey level of the board exposed to similar intensity on-axis light. This occurs because the board has a flat surface like the pads. The surface is, however, less mirror-like and will reflect less light in general.

Lastly, the paste reflects light more from increasing off-axis lighting than increasing on-axis lighting. Among the board, pad and paste, only paste exhibits this behavior. This behavior occurs because of the texture quality of the paste which scatters light in all directions, such that some off-axis light is reflected into the camera. The different response of paste can be identified and used to detect paste on boards.

Figure 7:
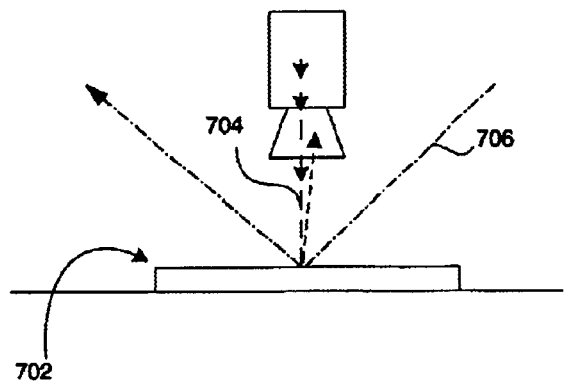
FIG. 7 illustrates light being reflected from a pad surface.

FIG. 7 illustrates light being reflected from a pad surface 702 As can be seen, most on-axis light 704 is reflected back into a camera 700. Off-axis light 706 is reflected elsewhere.

Figure 8:
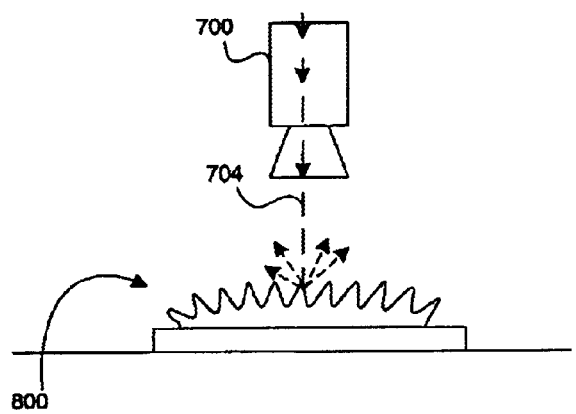
FIG. 8 illustrates light being reflected from a solder paste surface.

FIG. 8 illustrates light being reflected from a solder paste surface 800. On-axis light 704' is scattered due to the rough texture of the solder paste surface 800.

Figure 9:
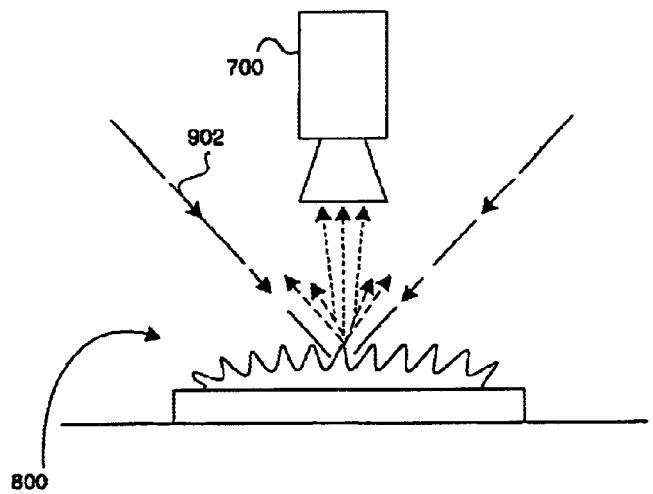
FIG. 9 is another view illustrates off-axis light being scattered due to a texture of the solder paste surface.

FIG. 9 illustrates off-axis light 902 being scattered due to the texture of the solder paste surface 800; however, off-axis light is illuminated from multiple sides, thus reflecting more light into the camera.

In an embodiment, this behavior is detected, for example, by taking two or more images having different off-axis and on-axis lighting and subtracting the two or more images to produce a difference image. Those locations in the difference image having a positive value are deemed to be representative of paste. Any regions where the difference of two pixels is negative are deemed not to be paste. For instance, using lighting states 3 and 13, subtracting them, and evaluating the sign of the pixels in the difference image provides identification of paste from the remainder of the image.

Optionally, an embodiment of the invention recognizes and uses an additional trend of behavior for increasing illumination for each type of material—that is the rate at which the reflectivity increases.

As shown in FIG. 1, the paste has a steep slope in a region of continuously increasing off-axis lighting (i.e. it saturates quickly from increasing off-axis lighting). The slope of the off-axis response is not only significant, it is also significantly greater than the rate of the change of the reflectivity response of the paste in the region of increasing on-axis lighting.

Unlike the paste, the board has a small slope in a region of continuously increasing off-axis lighting (i.e. it does not saturate quickly from increasing off-axis lighting). The slope of the off-axis response is not only insignificant, it is also less than the slope of the reflectivity response of the board in the region of increasing on-axis lighting.

Unlike paste or boards, the pads have less of a differentiation between the slope of the off-axis response when compared against the on-axis response.

This recognized different rate of response of paste can be identified and used to detect paste on boards.

In yet another embodiment, the method examines the rate of change of a single pixel value from a number of images, where each of the different images has a different lighting level.

To differentiate paste from board, the rate of change of a pixel representing paste from images under illuminations 11 and 13, for example, is higher than the rate of change of a pixel representing board from images under illuminations 11 and 13. In this example, paste is easily distinguished from board.

Differentiating paste from pad typically requires more than comparing the rate of changes of the two images under illuminations 11 and 13. In an embodiment, after identifying the two pixel positions (one for paste and one for pad in this example) exhibiting a high rate of change in the off-axis region, the rate of change for the same pixels in the on-axis region is generated. For example, the intensity of the pixels from two different images, such as an image under illuminations 3 and 6, are compared. If the rate of change in the on-axis region is approximately the same as the rate of change in the off-axis region, the pixel at that position is pad. If, however, the rate of change in the on-axis region is substantially less than the rate of change in the off-axis region, the pixel at that position is paste. In an alternate embodiment, it is not necessary to compute the rate of change of a second set of images. Instead, the rate of change between the two images under illuminations 11 and 13 is combined with the subtraction method described earlier. For example, the pixel represents paste if the magnitude in the off-axis region of one or more images is significantly greater than the on-axis region, and the pixel represents pad if the magnitude between the two images is approximately equal.

This extension of the subtraction technique can be used to discriminate between regions with more precision and can be used in cases where simple subtraction may be ambiguous.

It should be apparent that one or more reflectivity behaviors can be used for a given application. It should further be apparent that either one of the reflectivity behaviors can overrule the other for indeterminate cases, where the decision depends on the application.

It should be apparent that lighting states can be any combination of off-axis and on-axis lighting in each image. Zero against an increasing intensity was used herein, as an example.

Improvements to this method include removing artifacts that are caused by 3D relief of pad edges and circuit traces. An output of a difference image can be used to classify pixels as paste and as not paste. Thus, making the image primarily a binary image. Single pixel chains can be falsely detected as paste in the above image. Image processing, namely grey scale or binary morphology can be used to remove these artifacts. This technique is well-known in the art.

Figure 2:
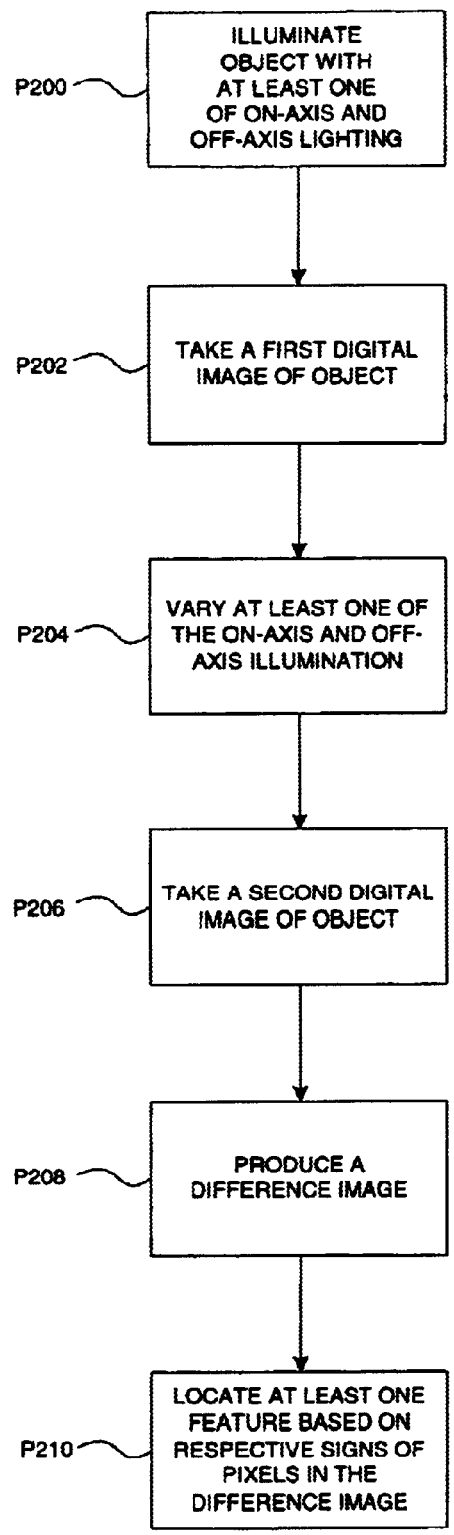
FIG. 2 is a flow chart showing the processing in a first embodiment of the invention.

FIG. 2 is a flow chart which explains the processing in an embodiment of the invention. At P200, an object, for example a circuit board, is illuminated with at least one of on-axis lighting and off-axis lighting.

At P202, a first digital image of the object is obtained.

At P204, the lighting is varied by changing an intensity of at least one of the on-axis lighting and off-axis lighting.

At P206, a second digital image of the object is acquired without moving a digital camera or the object from a position used to obtain the previous digital image.

At P208, a difference image is produced by subtracting one of the digital images from another.

At P210, at least one feature, for example solder paste, is located based on respective signs of gray levels of respective pixels in the difference image.

Figure 3:
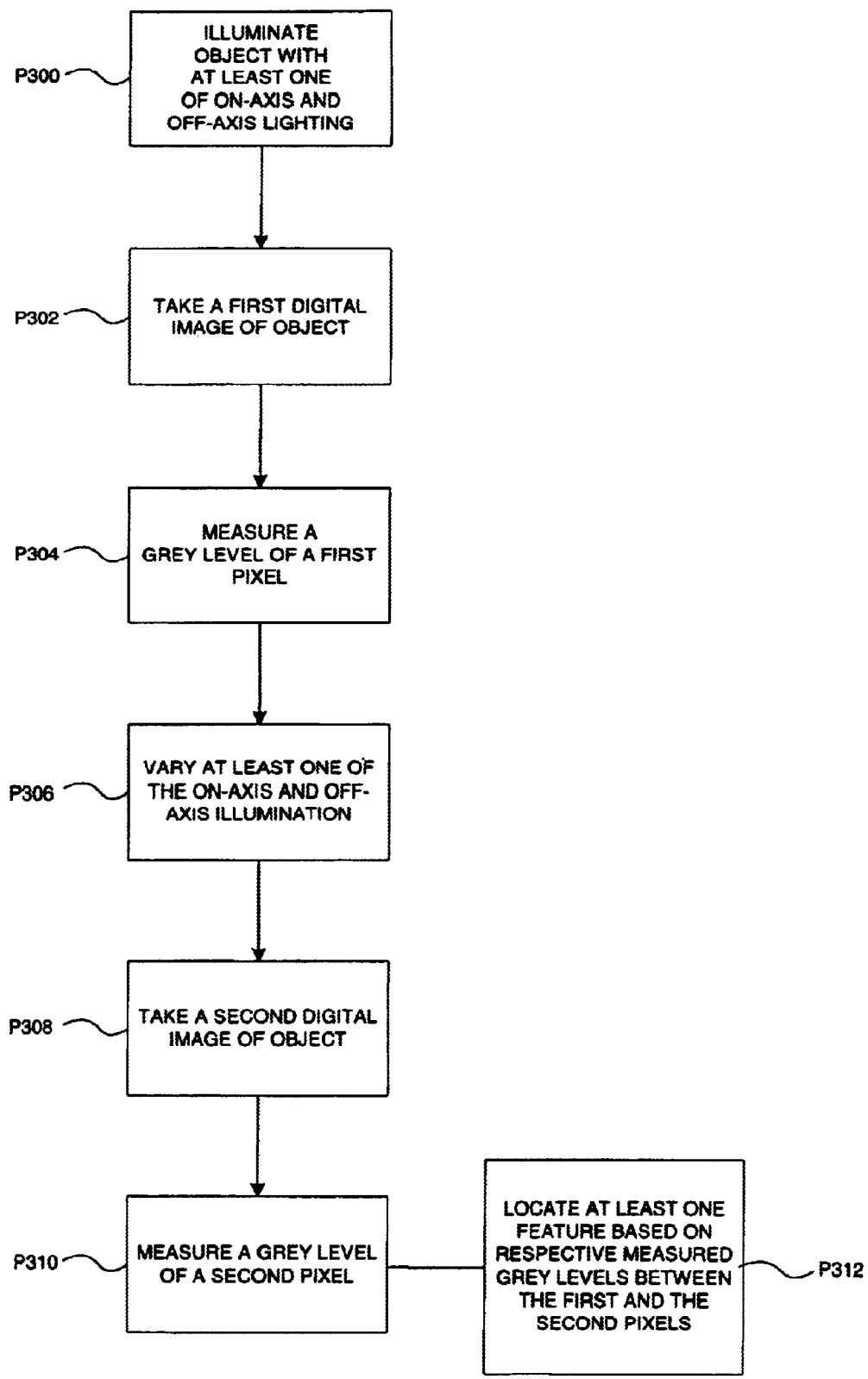
FIG. 3 is a flow chart showing the processing in a second embodiment of the invention.

FIG. 3 shows a flow chart which describes the processing in another embodiment of the invention.

At P300, an object is illuminated with at least one of on-axis lighting and off-axis lighting.

At P302, a first digital image of the object is obtained.

At P304, a gray level of a first pixel in a portion of the first digital image is measured.

At P306, at least one of the on-axis and the off-axis illumination is varied.

At P308, a second digital image of the object is obtained without moving a position of a digital camera and the object from a position in which they resided during the obtaining of the first digital image.

At P310, a gray level of a second pixel in a portion of the second digital image is measured.

At P312, at least one feature, for example, solder paste, is located based on respective measured gray levels between the first and the second pixels.

Figure 4:
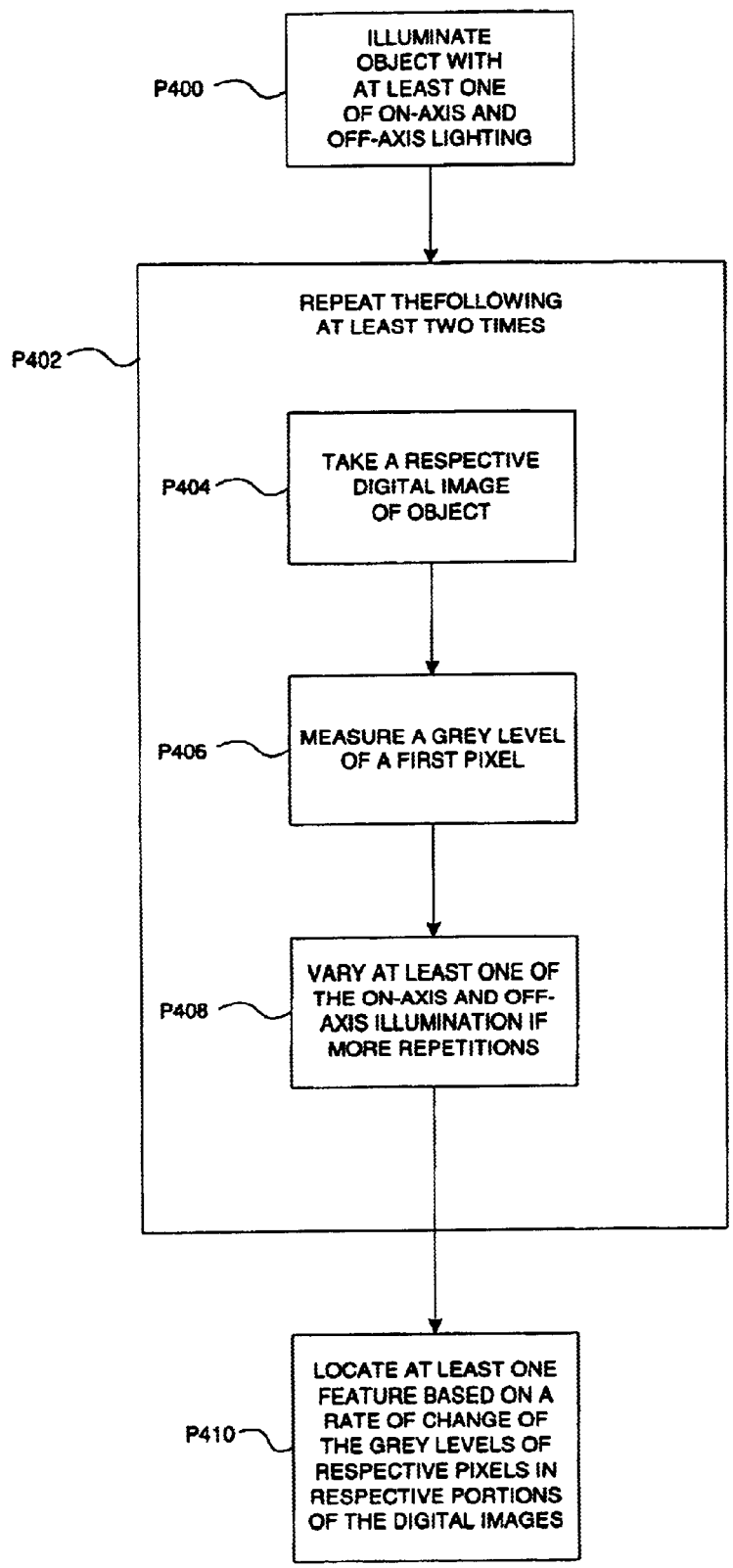
FIG. 4 is a flow chart showing the processing in a third embodiment of the invention.

FIG. 4 shows a flow chart illustrating processing in another embodiment of the invention.

At P400, the object is illuminated with at least one of on-axis lighting and off-axis lighting.

P402, shows processes P404 through P408 being repeated at least two times.

At P404, a respective digital image of the object is acquired.

At P406, a gray level of a first pixel is measured.

At P408, at least one of the on-axis and off-axis lighting is varied if more repetitions of processes 404 through 408 are to be performed.

At P410, at least one feature, for example, solder paste, is located based on a rate of change of the gray levels of respective pixels and respective portions of the obtained digital images.

Figure 5:
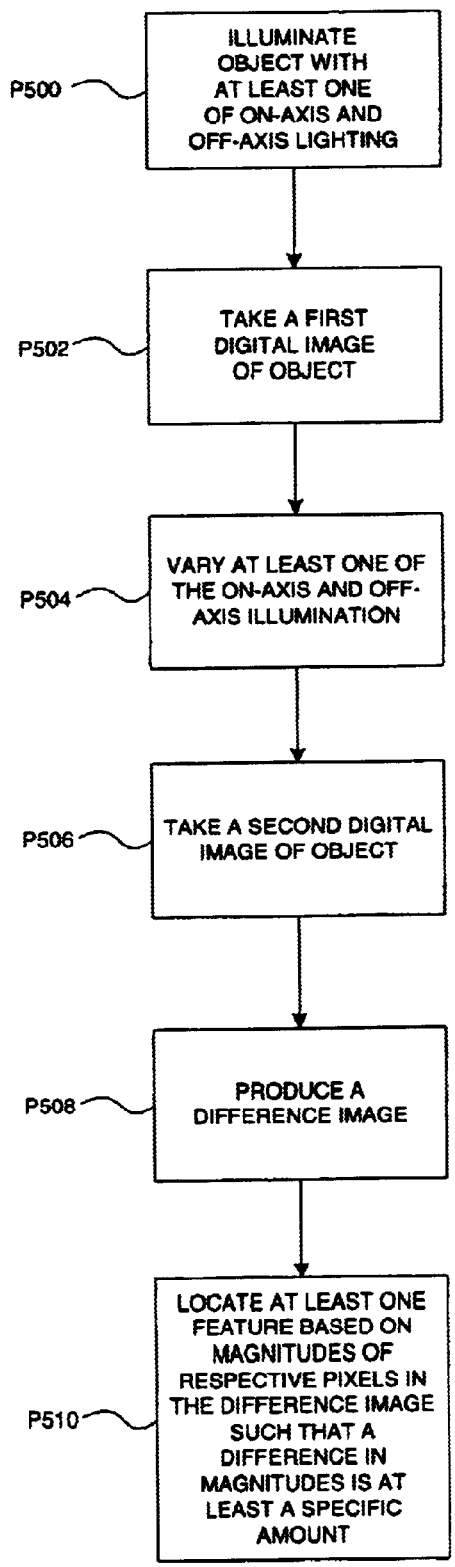
FIG. 5 is a flow chart showing the processing in a fourth embodiment of the invention.

FIG. 5 shows the processing in yet another embodiment of the invention.

At P500, the object is illuminated with at least one of on-axis and off-axis lighting.

At P502, a first digital image of the object is obtained.

At P504, an intensity of at least one of the on-axis lighting and the off-axis lighting is varied.

At P506, a second digital image of the object is obtained.

At P508, a difference image is produced by subtracting one of the first and the second digital image from another of the first and the second digital image.

At P510, at least one feature, for example, solder paste, is located based on magnitudes of gray levels of respective pixels in the difference image, such that a difference in magnitude is at least a specific amount.

Figure 6:
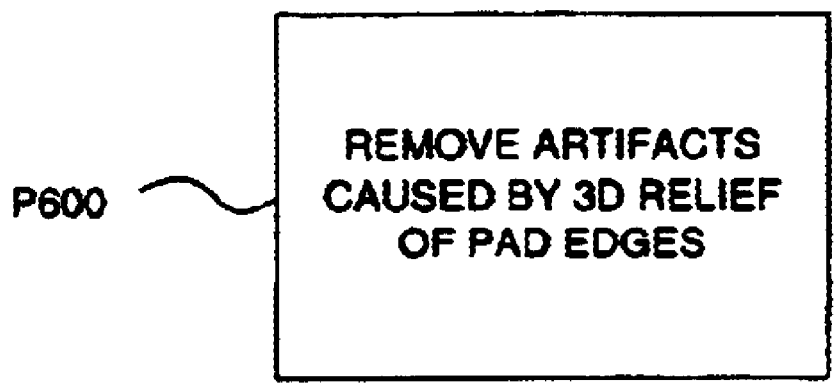
FIG. 6 shows a process to be used in a variation of the embodiments illustrated in FIGS. 2 through 5.

Each of the just-discussed methods can be improved at a post-processing act P600, shown in FIG. 6, and previously discussed, which removes artifacts caused by 3D relief of pad edges, after obtaining each of the digital images in the previous methods as shown in FIGS. 2–5. Act P600 can be performed by, for example, using morphology.

It should be apparent that the reflectivity properties of other components could be used for identification using the teachings disclosed herein.

It will be appreciated that although embodiments of the invention described in herein affect inspection of solder paste applied to printed circuit boards, it can be similarly implemented in processes to affect inspection of other materials such as screen printed adhesives, conductive adhesives or the like, applied on substrates other than printed circuit boards. Furthermore, the invention can be implemented and/or the inventive concepts herein modified to be used to inspect solder paste or adhesives applied in-line or applied in other ways. The invention extends to all equivalent structures, mechanisms, acts, and uses, such as are within the scope of the appended claims.

What is claimed is:

1. A method comprising:
   illuminating an object with at least one lighting source to provide at least one of on-axis illumination and off-axis illumination;
   repeating the following acts at least two times:
     acquiring a respective digital image of the object while a camera, the at least one lighting source, and the object are kept in a same position,
     measuring a grey level of a respective pixel representing a respective portion of the respective digital image, and
     varying a respective intensity of at least one of the on-axis illumination and the off-axis illumination when another repetition is to be performed;
   determining a rate of change of the grey levels of the respective pixels in the respective portions of the digital images; and
   locating at least one feature of the object using the determined rate of change.

2. The method of claim 1 wherein the object includes a circuit board and the at least one feature includes solder paste.

3. The method of claim 1 further comprising:
   removing artifacts caused by 3D relief of edges of items on the object.

4. The method of claim 1 further comprising:
   classifying the at least one feature using the determined rate of change.

5. The method of claim 4 wherein the object is a printed circuit board, and the at least one feature is solder paste.

6. A method comprising:
   illuminating an object with off-axis illumination;
   providing a first lighting condition wherein the off-axis illumination has a first intensity;
   acquiring a first image of the object;
   providing a second lighting condition wherein the off-axis illumination has a second intensity;
   acquiring a second image of the object;
   illuminating the object with on-axis illumination;
   providing a third lighting condition wherein the on-axis illumination has a first intensity;
   acquiring a third image of the object;
   providing a fourth lighting condition wherein the on-axis illumination has a second intensity;
   locating at least one feature of the object based on a rate of change in an intensity measurement of at least one respective pixel between the first and second image, and a rate of change in an intensity measurement of the at least one respective pixel between the third and fourth image.

* * * * *